United States Patent [19]
Robertson et al.

[11] Patent Number: 5,804,211
[45] Date of Patent: Sep. 8, 1998

[54] COMPOSITION AND METHOD FOR SUPPRESSING OR ELIMINATING SNORING

[75] Inventors: Lydia Robertson; Edward M. Harris, both of Little Rock, Ark.

[73] Assignee: Health Pharm USA, Inc., Little Rock, Ark.

[21] Appl. No.: 658,693

[22] Filed: Jun. 5, 1996

[51] Int. Cl.$^6$ .............................. A61F 13/02; A01N 65/00
[52] U.S. Cl. ........................................ 424/434; 424/195.1
[58] Field of Search ................................. 424/434, 195.1

[56] References Cited

U.S. PATENT DOCUMENTS

| | | |
|---|---|---|
| 4,551,473 | 11/1985 | Schossow . |
| 4,556,557 | 12/1985 | Reichert . |
| 4,668,513 | 5/1987 | Reichert . |
| 4,831,057 | 5/1989 | Reichert . |
| 5,302,583 | 4/1994 | Costa et al. . |
| 5,422,374 | 6/1995 | Miyao et al. . |
| 5,516,765 | 5/1996 | Andermann . |
| 5,565,201 | 10/1996 | Li . |

OTHER PUBLICATIONS

The Reader's Digest Association, Inc., Magic of Medicine of Plants, 1993, pp. 266,284, 341,373, 374.
Mayel, The Natural Health First–Aid Guide, 1994, pp. 37, 38, 56.
Weiner, The Herbal Bible, 1992, pp. 199,200, 207, 247, 294.
Ody, The Complete Medicinal Herbal, 1993.
Silent–Nite Advertisement, 1996.
Braver, et al., Chest, Treatment for Snoring, May 1995, pp. 1283–1288.
McIntyre, Herbs for Common Ailments, 1992, pp. 12, 20–25.
Leung, Encyclopedia of Common Natural Ingredients used in Food, Drugs and Cosmetics, 1980, pp. 184–186, 260–261.
Kingzett's Chemical Encyclopedia, 1966, pp. 455–446.
The Merck Index, 1989, p. 3288.
Murray, et al., Encyclopedia of Natural Medicine, 1991, p. 423.
Olshevsky et al., The Manual of Natural Therapy, 1989, p. 29.
Bricklin, The Practical Encyclopedia of Natural Healing, 1983, pp. 252–254.

*Primary Examiner*—Carlos Azpuru
*Attorney, Agent, or Firm*—Mark A. Rogers; Gary N. Speed; Mark M. Henry

[57] ABSTRACT

A composition and method are disclosed in which a solution comprising zingiber officinale, dioscorea and a salt are administered to a soft palate and uvula of a host. The solution preferably includes chamomile and a suitable delivery agent that will preferably hold the active ingredients in solution. The solution is preferably administered in the form of a throat spray or nose drop and may also include a flavoring agent.

18 Claims, No Drawings

COMPOSITION AND METHOD FOR SUPPRESSING OR ELIMINATING SNORING

BACKGROUND OF THE INVENTION

This invention relates to a composition and method for suppressing or eliminating snoring, and more particularly, to a topically applied composition and method for suppressing or eliminating snoring.

Snoring is a general term for loud sounds that a sleeper may make in the course of breathing. It is a problem that affects roughly 25 percent of men and women in the United States, including approximately 20 percent of men and 5 percent of women between the ages of 30 and 35 and 60 percent of men and 40 percent of women at age 60. The sounds of snoring are caused by low frequency vibrations of the pharyngeal structures, or air vibrating the soft palate, uvula, back of the tongue and other soft structures of the respiratory passage.

In recent years, snoring has come to be recognized as a more serious problem than previously believed. Studies suggest that snoring causes or is an indication of an increased risk of developing cardiovascular problems, including high blood pressure, heart attack, stroke and irregular heartbeats, and life expectancies appear to be shorter for people who snore. Although a person may not be aware of his or her snoring, the person's sleep may nonetheless be adversely affected. Snoring, even if it fails to wake the sleeper, appears to disrupt relaxation, dreams and the microstructure of sleep, resulting in fatigue, irritability and drowsiness during the following day.

Efforts to control snoring have taken many forms. For example, wrist alarms have been used to rouse a sleeper when the wrist alarm detects the sound of snoring; adhesive nasal strips have been used to help open the nostrils of a sleeper for improved breathing; septum stimulator devices have been used to grip or pinch the nerves of the septum in an effort to improve air flow through the nose; and specially shaped neck pillows have been proposed to realign the spine and relieve muscle stress during sleep. Surgery has also been used, such as laser-assisted uvulopalatoplasty which trims and reshapes the uvula and posterior soft palate and which requires three to four procedures spaced four to six weeks apart. Compositions for topical application have also been proposed, including eye drops, nose drops and mouthwashes.

SUMMARY OF THE INVENTION

It is therefore an object of the present invention to provide a composition and method for suppressing or eliminating snoring.

It is a further object of the present invention to provide a composition of the above type that may be topically applied to the soft palate and uvula to suppress or eliminate snoring.

It is a still further object of the present invention to provide a composition of the above type that may be easily manufactured.

It is a still further object of the present invention to provide a composition of the above type that uses natural active ingredients.

It is a still further object of the present invention to provide a composition of the above type that may be applied as a throat spray, nose drop, nasal mist, inhalant, mouthwash, swab or gargle.

It is a still further object of the present invention to provide a composition of the above type that may suppress or prevent snoring for hours or even days with a single application.

It is a still further object of the present invention to provide a composition of the above type that will open sinus and nasal passages.

It is a still further object of the present invention to provide a composition of the above type that acts as a vasoconstrictor in the nasal mucosa to relieve nasal congestion.

It is a still further object of the present invention to provide a composition of the above type that will reduce swelling of nasal passages and shrink swollen mucous membranes.

It is a still further object of the present invention to provide a composition of the above type that will cause extended contraction of muscles in the soft palate and uvula areas.

It is a still further object of the present invention to provide a composition of the above type that will cause constriction of the mucosa of the uvula and soft palate.

Toward the fulfillment of these and other objects and advantages, the composition and method of the present invention comprises administering to a soft palate and uvula of a host a solution comprising zingiber officinale, dioscorea and a salt. The solution preferably includes chamomile and a suitable delivery agent that will preferably hold the active ingredients in solution.

The solution may also be administered to the nasal cavity.

DETAILED DESCRIPTION OF THE PREFERRED EMBODIMENT

Snoring is a general term for the loud sounds that a sleeper may make in the course of breathing. The sounds are caused by air vibrating the soft palate, uvula, back of the tongue, and other soft structures of the respiratory passage, particularly when a sleeper is on his or her back and breathing through the mouth. A deviated septum or other obstructions can augment snoring, as can obesity and loss of muscle tone through such things as disease, alcoholism or aging. Snoring normally is not considered to be a health problem, but a severe case may indicate abnormal respiratory-passage growths, drug abuse or other problems to be addressed. Snoring may also be associated with sleep apnea, a sometimes life-threatening condition in which a sleeper experiences numerous non-breathing episodes.

The physiology of the mouth, soft palate, uvula and respiratory passages all impact the snoring phenomenon. The palate forms the roof of the human mouth and is composed of a hard palate in front and soft palate in back. The soft palate is of particular concern when attempting to suppress or eliminate snoring. The soft palate is a movable fold, suspended from the posterior border of the hard palate, and extending downward and backward between the oral and nasal parts of the pharynx. It consists of a fold of mucous membrane enclosing an aponeurosis, muscular fibers, vessels, nerves, lymphoid tissue and mucous glands.

In its normal position, relaxed and pendant, the anterior surface of the soft palate is concave and marked by a median raphe. Its posterior surface is convex and contiguous with the floor of the nasal cavity. Its superior border is attached to the posterior margin of the hard palate, and its sides are blended with the pharynx. Its inferior border is free. The lower portion of the soft palate hangs like a curtain between the mouth and the pharynx. The mucous membrane of the soft palate is thin and consists of stratified squamous epithelium excepting the upper part of its posterior surface and near the pharyngeal orifice of the auditory tube, where it is columnar and ciliated (respiratory epithelium) like that of the nasal cavities with which it is contiguous. Beneath the mucous membrane on both surfaces there are numerous palatine mucous glands which are most abundant on the oral surface and around the uvula. Taste buds are present in the epithelium of its oral surface. The veins in the palate end chiefly in the pterygoid and tonsillar plexuses. The lymph vessels pass to the deep cervical lymph nodes. The sensory nerves are derived from the greater and lesser palatine, and the nasopalatine and the glossopharyngeal nerves. The lesser palatine nerves contain taste fibers from the oral surface.

The palatopharyngeus extends from the soft palate to the pharyngeal wall and is covered by the mucous membrane of the palatopharyngeal arch. In the soft palate, it is arranged in two layers which enclose the levator veli palatini and the musculus uvulae. At the posterolateral part of the soft palate, the two layers blend and are joined posteriorly by the salpingopharyngeus muscle, a slender slip descending from the pharyngeal end of the auditory tube in close relation to the salpingopharyngeal fold.

The uvula is a small conical member that hangs from the middle of the lower border of the soft palate. It is a fold of mucous membrane enclosing fibrous aponeurosis and several muscles. The muscular substance of the soft palate region is composed of five pairs of muscles, the palatopharyngeus, muscular uvulae, levator veli palatini, tensor veli palatini and palatoglossus. Muscular tissue is of course comprised of long cells that contract when stimulated, to produce motion. In its anterior part, the uvula contains the palatine aponeurosis (muscle formed into flattened sheets, with broad, thin tendons or a flattened sheet of dense connective tissue covering certain muscles) which is attached in front to the posterior border of the bony palate and on each side to the pharyngobasilar fascia and fades away posteriorly. The palatine aponeurosis is derived mainly from the tendons of the two tensor muscles; the other muscles, with the exception of the palatoglossus, are inserted into it.

The musculus uvulae is a slender bundle of muscles which lies alongside its fellows, between the layers of the palatopharyngeus and above the levator veli palatini. Both bundles arise from the nasal spine and the palatine aponeurosis, and they unite as they proceed backward to end in the mucous membrane of the uvula. It is a bilateral structure, arising from the posterior nasal spine of the palatine bones and from the palatine aponeurosis, between the two laminae of which the two uvular muscles lie; it descends to be inserted into the mucous membrane of the uvula. The musculus uvulae pulls up and contracts the uvula on its own side.

Certain dermis cells such as those that are found in the region of the soft palate and uvula release chemicals such as histamine, bradykinin and various prostaglandins. These cause local changes in capillary diameter (redness and warmth), capillary permeability (swelling) and stimulation of appropriate nerve endings (pain), all signs of inflammation. The epidermis lacks blood vessels and obtains its nutrition by diffusion from capillaries in the dermis.

1. The tissue covering the soft palate and uvula is epithelial tissue which covers the surface of an animal and the lining of its tubes for digestion and respiration. The muscle tissue of the soft palate is skeletal and is controlled by the central nervous system and, to a certain extent, by will. Also present is nervous tissue, connective tissue and fluid tissue such as blood and lymph, both of which are present in the soft palate.

The symptom of snoring is often caused, at least in part, by an inflammation or enlargement of the tissues in the soft palate. The inflammation or enlargement may result from any number of causes; in general, a dynamic, complex of cytologic and histologic reactions occur in the affected blood vessels and adjacent tissues in response to an injury or abnormal stimulation caused by physical, chemical or biologic agents. The present composition and method attempts to suppress or eliminate the symptom of snoring by addressing at least some of the root causes.

The active ingredients of the present solution are zingiber officinale, dioscorea and a salt. Another active ingredient, chamomile, is preferably included. The active ingredients are preferably held in solution by a suitable delivery agent that includes propylene glycol, water and glycerine, and a flavoring agent is preferably added. Ethyl alcohol may also be present in the solution because the active ingredients are preferably obtained as extracts suspended in ethyl alcohol. The solution is administered to the soft palate and uvula, preferably in the form of a throat spray or nose drop. When in the form of a nose drop, the solution also preferably includes an antimicrobial agent such as benzalkonium chloride.

As used herein, zingiber officinale refers to the various members of the ginger family, known under many, occassionally overlapping or duplicative, names including but not limited to zingiber officinale, zingiber officinalis, zingiberaceae, ginger, gingerroot, shringara and zingiberis. It is preferably obtained in the form of an extract of dried root or rhizome but may be obtained in any number of forms, including but not limited to dried or fresh root or rhizome, essential oil or extracts of the above. The extract is preferably in a Menstruum ratio of 1:5, or 1 g of dried root or rhizome per 5 milliliters of solvent, such as ethyl alcohol. The zingiber officinale is preferably present in the solution in a weight percent substantially within a range of approximately 1.0 to approximately 0.01, is more preferably substantially within a range of approximately 0.5 to approximately 0.05, and is most preferably substantially within a range of approximately 0.2 to approximately 0.07.

As used herein, dioscorea refers to the various members of the yam family, known under many, occassionally overlapping or duplicative, names including but not limited to dioscoreaceae, dioscorea villosa, dioscorea hypoglauca, dioscorea opposita, yam, wild yam, Mexican wild yam, colic root, rheumatism root and devil's-bones. It is preferably obtained in the form of an extract of dried root or rhizome but may be obtained in any number of forms, including but not limited to dried or fresh root or rhizome, essential oil or extracts of the above. The extract is preferably in a Menstruum ratio of 1:5, or 1 g of dried root or rhizome per 5 milliliters of solvent, such as ethyl alcohol. The dioscorea is preferably present in the solution in a weight percent substantially within a range of approximately 0.4 to approximately 0.01, is more preferably substantially within a range of approximately 0.2 to approximately 0.02, and is most preferably substantially within a range of approximately 0.1 to approximately 0.03.

As used herein, chamomile refers to the various members of the chamomile family, known under many, occassionally overlapping or duplicative, names including but not limited to Roman chamomile, German chamomile, common chamomile, English chamomile, true chamomile, chamomilla, chamaemelum nobile, anthemis nobilis, matricaria recutita, matricaria chamomilla, Kamillen, Camomille, and Manzanilla. The chamomile is preferably matricaria chamomilla and is preferably obtained as an extract of fresh flowers in a Menstruum ratio of 1:1.25 (1 g of fresh flower per 1.25 mL of solvent, such as ethyl alcohol). The chamomile may of course be obtained in any number of forms, including but not limited to fresh flower, dried flower, essential oil or extracts of the above. The chamomile is preferably present in the solution in a weight percent substantially within a range of approximately 0.8 to approximately 0.01, is more preferably substantially within a range of approximately 0.4 to approximately 0.04, and is most preferably substantially within a range of approximately 0.2 to approximately 0.06.

Although the solution appears to be more effective with chamomile included, chamomile may be deleted altogether or other components may be substituted in place of chamomile. For example, an early formula for the solution used a passionflower instead of chamomile. The passionflower family includes such members known by many, often overlapping or duplicative, names such as passifloraceae, passiflora incarnata, apricot vine, maypop, passion vine, purple passionflower, and wild passionflower. Although not preferred, as indicated below in connection with a discussion of a double blind study, the solution including passionflower was considered highly effective.

Although any number of salts or electrolytes may be used, the salt used is preferably sodium chloride or potassium chloride and is more preferably sodium chloride. The salt is preferably present in the solution in a weight percent substantially within a range of approximately 2.0 to approximately 0.02, is more preferably substantially within a range of approximately 1.0 to approximately 0.1, and is most preferably substantially within a range of approximately 0.4 to approximately 0.15.

The delivery agent comprises propylene glycol, glycerine and water, and, particularly for the nose drop, may include an antimicrobial and preservative such as benzalkonium chloride. The delivery agent places the active ingredients in a convenient form for administering to the desired areas and improves absorption by coating the treated tissue with the active ingredients. The delivery agent preferably also holds the active ingredients in solution and acts as a preservative and an antimicrobial. The combination of delivery agents was also selected in part to ensure that all active ingredients would be held in solution in acceptable amounts and for an extended period of time. The propylene glycol is preferably present in the solution in a weight percent substantially within a range of approximately 60 to approximately 20, is more preferably substantially within a range of approximately 50 to approximately 30, and is most preferably substantially within a range of approximately 45 to approximately 35. The glycerine is preferably present in the solution in a weight percent substantially within a range of approximately 60 to approximately 10, is more preferably substantially within a range of approximately 30 to approximately 15, and is most preferably substantially within a range of approximately 25 to approximately 20. The water is preferably present in the solution in a weight percent substantially within a range of approximately 60 to approximately 20, is more preferably substantially within a range of approximately 45 to approximately 25, and is most preferably substantially within a range of approximately 40 to approximately 30. If used, the benzalkonium chloride is preferably present in the solution in a weight percent substantially within a range of approximately 0.1 to approximately 0.001, and is more preferably approximately 0.001.

It is understood that any number of suitable delivery agents may be used, including but not limited to water, vegetable glycerin in combination with water (such as in Example 4, below), or an alcohol-based delivery agent.

Particularly for the throat spray, a flavoring agent, including but not limited to wintergreen, peppermint, cinnamon or similar oils or sorbitol may be used. If used, the flavoring agent is preferably present in the solution in a weight percent substantially within a range of approximately 1 to approximately 0.01, is more preferably substantially within a range of approximately 0.5 to approximately 0.02, and is most preferably substantially within a range of approximately 0.15 to approximately 0.03.

As mentioned earlier, because three of the active ingredients are preferably obtained by blending an extract including ethyl alcohol into the solution, ethyl alcohol will of course be present in the solution. Dictated largely by the desired strength or concentration of the various active ingredients, the ethyl alcohol is preferably present in the solution in a weight percent substantially within a range of approximately 6.0 to approximately 0.06, is more preferably substantially within a range of approximately 3.0 to approximately 0.3, and is most preferably substantially within a range of approximately 1.0 to approximately 0.4.

The following are examples of solutions found to be effective. Examples 1 through 3 reflect presently preferred versions of the solution, and Example 4 reflects an earlier version of the solution that, although not presently preferred, is considered to be effective.

EXAMPLE 1: NOSE DROP

One liter of the nose drop solution is prepared using the following starting materials:

| | |
|---|---|
| ginger extract (1:5) | 7.5 mL |
| wild yam extract (1:5) | 3.0 mL |
| chamomile extract (1:1.25) | 1.5 mL |
| propylene glycol USP | 400 mL |
| glycerine | 200 mL |
| sodium chloride USP | 2 g |
| benzalkonium chloride 50% NF | 0.02 mL |
| purified water | 388 mL |

To prepare one liter of the nose drop solution, the propylene glycol is poured into a suitable container and the ginger extract, wild yam extract and chamomile extract are added while stirring. Glycerine is then added while stirring, and the solution is stirred until completely blended. A separate solution is prepared by dissolving the sodium chloride and benzalkonium chloride in approximately 200 mL purified water, and this solution is added to the other solution and stirred for approximately 10 minutes. A sufficient quantity of water is then added to bring the volume of the solution to 1.0 L, and this solution is stirred for approximately 10 minutes. The resulting solution has the following composition:

| Component | Mass/Volume | Weight Percent |
|---|---|---|
| zingiber officinale | 1.5 g | 0.14 |
| dioscorea villosa | 0.6 g | 0.06 |
| matricaria chamomilla | 1.2 g | 0.11 |
| sodium chloride | 2 g | 0.19 |
| propylene glycol | 400 mL | 38.73 |
| glycerine | 200 mL | 23.57 |
| purified water | 388 mL | 36.28 |
| ethyl alcohol | 12 mL | 0.90 |
| benzalkonium chloride 50% NF | 0.02 mL | 0.001 |

EXAMPLE 2: WINTERGREEN FLAVORED THROAT SPRAY

One liter of a solution for use as a wintergreen flavored throat spray is prepared using the following starting materials:

| | | |
|---|---|---|
| ginger extract (1:5) | 5 mL | |
| wild yam extract (1:5) | 2 mL | |
| chamomile extract (1:1.25) | 1 mL | |
| propylene glycol USP | 400 mL | |
| glycerine | 200 mL | |
| sodium chloride USP | 2 g | |
| purified water | 391 mL | |
| wintergreen oil NF | 1 mL | |

To prepare one liter of the solution for use as a wintergreen flavored throat spray, the propylene glycol is poured into a suitable container and the ginger extract, wild yam extract and chamomile extract are added while stirring. Glycerine is then added while stirring, and the solution is stirred until completely blended. Wintergreen oil is then added and the solution is stirred until completely blended. A separate solution is prepared by dissolving the sodium chloride in approximately 200 mL purified water, and this solution is added to the other solution and stirred for approximately 10 minutes. A sufficient quantity of water is then added to bring the volume of the solution to 1.0 L, and this solution is stirred for approximately 10 minutes. The resulting solution has the following composition:

| Component | Mass/Volume | Weight Percent |
|---|---|---|
| zingiber officinale | 1 g | 0.09 |
| dioscorea villosa | 0.4 g | 0.04 |
| matricaria chamomilla | 0.8 g | 0.08 |
| sodium chloride | 2 g | 0.19 |
| propylene glycol | 400 mL | 39.28 |
| glycerine | 200 mL | 24.27 |
| purified water | 391 mL | 35.34 |
| ethyl alcohol | 8 mL | 0.60 |
| wintergreen oil NF | 1 mL | 0.11 |

Example 3: PEPPERMINT FLAVORED THROAT SPRAY

One liter of a solution for use as a peppermint flavored throat spray is prepared using the following starting materials:

| | | |
|---|---|---|
| ginger extract (1:5) | 5 mL | |
| wild yam extract (1:5) | 2 mL | |
| chamomile extract (1:1.25) | 1 mL | |
| propylene glycol USP | 400 mL | |
| glycerine | 200 mL | |
| sodium chloride USP | 2 g | |
| purified water | 391.5 mL | |
| peppermint oil USP | 0.5 mL | |

To prepare one liter of the solution for use as a peppermint flavored throat spray, the propylene glycol is poured into a suitable container and the ginger extract, wild yam extract and chamomile extract are added while stirring. Glycerine is then added while stirring, and the solution is stirred until completely blended. Peppermint oil is then added and the solution is stirred until completely blended. A separate solution is prepared by dissolving the sodium chloride in approximately 200 mnL purified water, and this solution is added to the other solution and stirred for approximately 10 minutes. A sufficient quantity of water is then added to bring the volume of the solution to 1.0 L, and this solution is stirred for approximately 10 minutes. The resulting solution has the following composition:

| Component | Mass/Volume | Weight Percent |
|---|---|---|
| zingiber officinale | 1 g | 0.09 |
| dioscorea villosa | 0.4 g | 0.04 |
| matricaria chamomilla | 0.8 g | 0.08 |
| sodium chloride | 2 g | 0.19 |
| propylene glycol | 400 mL | 39.28 |
| glycerine | 200 mL | 24.27 |
| purified water | 391.5 mL | 35.39 |
| ethyl alcohol | 8 mL | 0.60 |
| peppermint oil USP | 0.5 mL | 0.06 |

EXAMPLE 4: COMPOSITION OF EARLY VERSION OF NOSE DROP

An early version of the nose drop that is effective but that is not presently preferred used approximately 4.5 mnL ginger root extract (1:5), approximately 2.25 mL wild yam extract (1:5), approximately 2.5 mL matricaria chamomilla extract (1:1.25), approximately 4.5 g sodium chloride, approximately 80 mnL vegetable glycerin and approximately 906.25 niL purified water.

In use, the solution is administered to the soft palate and uvula of a user, and possibly to the nasal cavity. For the nose drops, 2 to 4 drops are placed in each nostril of the user shortly before sleeping, preferably with the user lying flat with the head tilted back for insertion of the dropper tip. As the drops drain from the nasal cavity, the drops contact and coat the soft palate and uvula of the user. The user should remain lying to assist the drops in draining through to the throat and to thereby obtain a better application of the solution to the soft palate and uvula. Particularly with the nose drops, there may be an immediate tingling sensation when the drops are placed in the nostril, but all such sensation should pass within a few seconds. Storing the product in a refrigerator may decrease this tingling sensation.

For the throat spray, the user should aim one spray directly at the uvula, one spray to the right of the uvula and one spray to the left of the uvula, thereby applying an effective amount of the solution to the soft palate and uvula. If a stronger dosage of the throat spray is desired, the 3 sprays may be repeated. The minimum dosage of 2 drops in each nostril for the nose drops or 3 sprays for the throat spray should be used initially, and the dosage can later be increased to 4 drops per nostril or 6 sprays of the throat spray if desired by the user. After achieving satisfactory results, the user may skip a progressive number of nights to determine how long optimum results can be maintained without reapplication of the solution. A number of users have claimed that after using the solution for approximately 3 to 5 nights, they are able to skip up to 7 nights before needing to reapply the solution. Of course, minimum and maximum dosages may vary significantly from user to user and depending upon such things as the concentrations of the active ingredients, the delivery agent used, and the method and efficiency of application.

The active ingredients are rapidly absorbed following administration, and the delivery agent provides for improved activity of the solution by maintaining the active ingredients in solution for delivery and by coating the tissue to hold the active ingredients in contact with the tissue for an extended period of time. Onset of action typically occurs within approximately 5 to 10 minutes of application, with peak effects attained in approximately 30 minutes. Duration of the effectiveness of the solution is generally 12 to 24 hours, but can be considerably longer, such as for a period of up to a week.

It is believed that the solution may directly affect the uvula by shrinking the muscular tissue or fluid tissue of the soft palate and uvula areas. It may act on α receptors in the mucosa of the respiratory tract, producing vasoconstriction which results in shrinkage of swollen mucous membranes, reduction of tissue, hyperemia, edema and nasal congestion and an increase in nasal airway patency. The solution seems to serve as a blocking agent, interfering with the action of histamine, primarily in capillaries surrounding mucous tissues and sensory nerves of nasal and adjacent areas. Also, following oral or nasal administration, constriction of blood vessels in the nasal mucosa may relieve nasal congestion. The solution may also antagonize some of the skeletal muscle in the soft palate and uvula, stimulating actions of anti-histamine.

It is also believed that the solution may produce or contribute to extended contractions of the muscles of the soft palate and uvula, possibly lasting for days in some individuals. In that regard, smooth muscles, such as those found in the walls of the digestive tract and those forming the soft palate and uvula are generally not subject to voluntary control but are instead controlled by the autonomic nervous system. Smooth muscles contract rather slowly but can remain contracted for extended periods of time. Muscle contraction begins when the sarcolemma receives an impulse from a motor neuron. The impulse changes the permeability of the sarcoplasmic reticulum throughout the fiber. The reticulum is loaded with calcium and releases the $Ca_2$ into the muscle cytoplasm. A series of activity occurs finally bringing the muscle into its fully shortened state. As long as calcium ions are present and ATP is available, the contracted state will hold. Calcium ions appear to be the controlling factor in extended muscle contraction. Thus, it is believed that the present solution may affect the presence of calcium ions in the muscles, such as by stimulating production or increasing the duration that such ions remain in the muscles of the soft palate and uvula. The solution therefore appears to cause or contribute to extended contractions of the soft palate and uvula, lasting for days in some individuals.

In a double blind study, 170 people responded to a newspaper advertisement seeking participants who suffered from snoring. The participants were not charged or compensated for participating in the study. The participants were informed that they would be provided with either an active product or a placebo. The active product supplied to participants was a nose drop similar to the solution described in Example 4, above, except that passionflower was used in place of chamomile.

Of the 170 people selected to participate, 68 people used the product or a placebo and responded to the survey, including 64 people who used the active product and 4 people who used the placebo. Of the 64 people responding who used the active product, 12 stopped snoring totally, 13 saw much improvement, 18 saw somewhat of an improvement and 23 saw no improvement. Of the 4 people who used the placebo, 1 saw improvement and 3 saw no improvement. The remaining 102 people selected did not respond to the survey. Of the people responding to the survey who were provided with the active product, over 65 percent saw at least some improvement, which compares very favorably to success rates claimed by other products for suppressing snoring. Since changing to the above-described preferred formulae, the positive feedback has increased significantly, typically in the form of positive responses in response cards provided with the product.

The solution is intended for the treatment of snoring caused by vibration of the tissues of the soft palate, uvula and respiratory tract and is not designed to treat sleep apnea or other serious sleep disorders and is not designed to provide relief from snoring caused by intra-nasal damage such as scar tissue or a deviated septum or caused by other congenital deformities. The solution should not be used by children under 12 years of age, by pregnant or nursing mothers or by those suffering from nasopharyngeal irritation or infection. The solution is also not intended for pets.

Modifications, changes and substitutions are intended in the foregoing, and in some instances, some features of the invention will be employed without a corresponding use of other features. For example, although the delivery agent is described as having propylene glycol, glycerine and water, water alone could be used or an alcohol based preservative/delivery agent could be used. Also, although the solution is described as being blended, the solution may be prepared in any number of ways. For example, an early, effective but non-preferred version of the formula was prepared using steps including boiling and autoclaving. Further, the strengths or concentrations of the various components may be adjusted over a relatively broad range. Further still, although the zingiber officinale, dioscorea and chamomile are preferably obtained in extract form for blending, any suitable source or form of the materials may be used. Further still, although nose drops and throat sprays are preferred manners of applying the solution, any other suitable means of topically applying the solution to the soft palate and uvula may be used, including but not limited to nasal sprays or inhalants, gargles and mouthwashes. Of course the above examples, masses, volumes, weight percentages, dosages and similar figures are given by way of example only and should not be construed as limiting the scope of the invention. Accordingly, it is appropriate that the appended claims be construed broadly and in a manner consistent with the scope of the invention.

What is claimed is:

1. A method for suppressing snoring, comprising administering to a soft palate and uvula of a host a solution comprising zingiber officinale, dioscorea, chamomile and a salt.

2. The method of claim 1 wherein said dioscorea comprises dioscorea villosa, said chamomile comprises matricaria chamomilla and said salt is selected from the group consisting of sodium chloride and potassium chloride.

3. The method of claim 2 wherein:
said zingiber officinale is present in said solution in a weight percent substantially within a range of approximately 1.0 to approximately 0.01;
said discorea villosa is present in said solution in a weight percent substantially within a range of approximately 0.4 to approximately 0.01;
said matricaria chamomilla is present in said solution in a weight percent substantially within a range of approximately 0.8 to approximately 0.01; and
said salt is present in said solution in a weight percent substantially within a range of approximately 2.0 to approximately 0.02.

4. The method of claim 2 wherein:
said zingiber officinale is present in said solution in a weight percent substantially within a range of approximately 0.5 to approximately 0.05;
said discorea villosa is present in said solution in a weight percent substantially within a range of approximately 0.2 to approximately 0.02;
said matricaria chamomilla is present in said solution in a weight percent substantially within a range of approximately 0.4 to approximately 0.04; and said salt is present in said solution in a weight percent substantially within a range of approximately 1.0 to approximately 0.1.

5. The method of claim 2 wherein:

said zingiber officinale is present in said solution in a weight percent substantially within a range of approximately 0.2 to approximately 0.07;

said discorea villosa is present in said solution in a weight percent substantially within a range of approximately 0.1 to approximately 0.03;

said matricaria chamomilla is present in said solution in a weight percent substantially within a range of approximately 0.2 to approximately 0.06; and said salt is present in said solution in a weight percent substantially within a range of approximately 0.4 to approximately 0.15.

6. The method of claim 1 further comprising administering said solution to a nasal cavity of said host.

7. The method of claim 1 wherein said solution is administered in the form of a throat spray.

8. The method of claim 1 wherein said solution is administered in the form of a nose drop.

9. The method of claim 1 wherein said solution further comprises a delivery agent, comprising propylene glycol and water.

10. The method of claim 1 wherein said solution further comprises a delivery agent, comprising propylene glycol and water.

11. The method of claim 10 wherein said solution further comprises a flavoring agent and wherein said delivery agent further comprises glycerine.

12. The method of claim 11 wherein:

said zingiber officinale is present in said solution in a weight percent substantially within a range of approximately 0.5 to approximately 0.05;

said discorea is present in said solution in a weight percent substantially within a range of approximately 0.2 to approximately 0.02;

said chamomile is present in said solution in a weight percent substantially within a range of approximately 0.4 to approximately 0.04;

said salt is present in said solution in a weight percent substantially within a range of approximately 1.0 to approximately 0.1;

said propylene glycol is present in said solution in a weight percent substantially within a range of approximately 60 to approximately 20;

said water is present in said solution in a weight percent substantially within a range of approximately 60 to approximately 20;

said glycerine is present in said solution in a weight percent substantially within a range of approximately 35 to approximately 15; and said flavoring agent is present in said solution in a weight percent substantially within a range of approximately 0.5 to approximately 0.05.

13. The method of claim 12 wherein said delivery agent further comprises benzalkonium chloride, said benzalkonium chloride being present in said solution in a weight percent substantially within a range of approximately 0.1 to 0.001.

14. A solution for suppressing snoring, comprising zingiber officinale, dioscorea, chamomile a salt and a delivery agent.

15. The solution of claim 14 wherein said delivery agent comprises propylene glycol, water and glycerine and wherein:

said zingiber officinale is present in said solution in a weight percent substantially within a range of approximately 0.5 to approximately 0.05;

said discorea is present in said solution in a weight percent substantially within a range of approximately 0.2 to approximately 0.02;

said chamomile is present in said solution in a weight percent substantially within a range of approximately 0.4 to approximately 0.04;

said salt is present in said solution in a weight percent substantially within a range of approximately 1.0 to approximately 0.1;

said propylene glycol is present in said solution in a weight percent substantially within a range of approximately 60 to approximately 20;

said water is present in said solution in a weight percent substantially within a range of approximately 60 to approximately 20; and said glycerine is present in said solution in a weight percent substantially within a range of approximately 35 to approximately 15.

16. A method for suppressing snoring, comprising administering to a soft palate and uvula of a host a solution consisting essentially of zingiber officinale, dioscorea, a salt, chamomile and a delivery agent.

17. The method of claim 16 wherein said dioscorea is dioscorea villosa, said salt is selected from the group consisting of sodium chloride and potassium chloride, and said chamomile is matricaria chamomilla.

18. The method of claim 17 wherein:

said zingiber officinale is present in said solution in a weight percent substantially within a range of approximately 0.2 to approximately 0.07;

said discorea villosa is present in said solution in a weight percent substantially within a range of approximately 0.1 to approximately 0.03;

said matricaria chamomilla is present in said solution in a weight percent substantially within a range of approximately 0.2 to approximately 0.06; and said salt is present in said solution in a weight percent substantially within a range of approximately 0.4 to approximately 0.15.

* * * * *